(12) United States Patent
Cheng et al.

(10) Patent No.: US 10,859,564 B2
(45) Date of Patent: Dec. 8, 2020

(54) METASTASIS MIMETIC DEVICE

(71) Applicant: University of Kansas, Lawrence, KS (US)

(72) Inventors: Nikki Cheng, Prairie Village, KS (US); Wei Bin Fang, Prairie Village, KS (US); Terry N. Faddis, Lawrence, KS (US); John Preston White, III, Overland Park, KS (US)

(73) Assignee: University of Kansas, Lawrence, KS (US)

( * ) Notice: Subject to any disclaimer, the term of this patent is extended or adjusted under 35 U.S.C. 154(b) by 923 days.

(21) Appl. No.: 14/765,754

(22) PCT Filed: Feb. 4, 2014

(86) PCT No.: PCT/US2014/014725
§ 371 (c)(1),
(2) Date: Aug. 4, 2015

(87) PCT Pub. No.: WO2014/121289
PCT Pub. Date: Aug. 7, 2014

(65) Prior Publication Data
US 2015/0369796 A1  Dec. 24, 2015

Related U.S. Application Data

(60) Provisional application No. 61/849,875, filed on Feb. 4, 2013.

(51) Int. Cl.
*G01N 33/50* (2006.01)
*B01L 3/00* (2006.01)
(Continued)

(52) U.S. Cl.
CPC .......... *G01N 33/5011* (2013.01); *B01L 3/502* (2013.01); *C12M 21/08* (2013.01);
(Continued)

(58) Field of Classification Search
CPC ..... B01L 2300/0681; B01L 2300/0803; B01L 2400/0472; B01L 2400/0644;
(Continued)

(56) References Cited

U.S. PATENT DOCUMENTS

2001/0031480 A1* 10/2001 Deisboeck ............. C12M 41/36
435/40.5
2013/0210131 A1* 8/2013 Renken .................. C12M 25/04
435/289.1

FOREIGN PATENT DOCUMENTS

KR   10-2006-0127003   12/2006

OTHER PUBLICATIONS

Shin, Min Kveong et al., "Integration of intra-and extravasation in one cell-based microfluidic chip for the study of cancer metastasis", Lab on a Chip, 2011, vol. 11, No. 22. pp. 3880-3887.
(Continued)

*Primary Examiner* — Gautam Prakash
*Assistant Examiner* — Lydia Edwards
(74) *Attorney, Agent, or Firm* — Ray Quinney & Nebeker P.C.; Paul N. Taylor

(57) ABSTRACT

Implementations of the present invention relate to apparatuses, systems, and methods for constructing and using a metastatic mimetic device. The device includes at least one chamber with a gate structure that allows a channel to selectively allow fluid communication between an interior of the chamber and an exterior of the chamber. The channel includes a porous member extending across a cross-section of the channel to control flow rates or allow the mimetic device to replicate transport across a member.

14 Claims, 5 Drawing Sheets

(51) Int. Cl.
*C12M 3/00* (2006.01)
*C12M 1/12* (2006.01)
*C12M 1/00* (2006.01)

(52) U.S. Cl.
CPC ............ *C12M 23/04* (2013.01); *C12M 23/34* (2013.01); *B01L 2300/0681* (2013.01); *B01L 2300/0803* (2013.01); *B01L 2400/0472* (2013.01); *B01L 2400/065* (2013.01); *B01L 2400/0644* (2013.01); *G01N 2500/10* (2013.01); *G01N 2800/7028* (2013.01)

(58) Field of Classification Search
CPC ... B01L 2400/065; B01L 3/502; C12M 21/08; C12M 23/04; C12M 23/34; G01N 2500/10; G01N 2800/7028; G01N 33/5011
USPC .................................................. 435/29, 288.7
See application file for complete search history.

(56) References Cited

OTHER PUBLICATIONS

Chaw, K. C. et al., "Multi-step microfluidic device for studying cancer metastasis". Lab on a Chip, 2007, vol. 7. No. 8, pp. 1041-1047.

Fu, Yi et al., "Nuclear deformation during breast cancer cell transmigration". Lab on a Chip, 2012. vol. 12. No. 19, pp. 3774-3778.

Huh, Dongeun et al., "From 3D cell culture to organs-on-chips", Trends in Cell Biology, 2011, vol. 21, No. 12, pp. 745-754.

Jeon, Jessie. S. et al., In vitro model of tumor cell extravasation, PloS One, Epub Feb. 20, 2013, vol. 8, No. 2, Article No. e56910 (internal pp. 1-9).

PCT/US2014/014725, dated Aug. 26, 2014, International Search Report and Written Opinion.

* cited by examiner

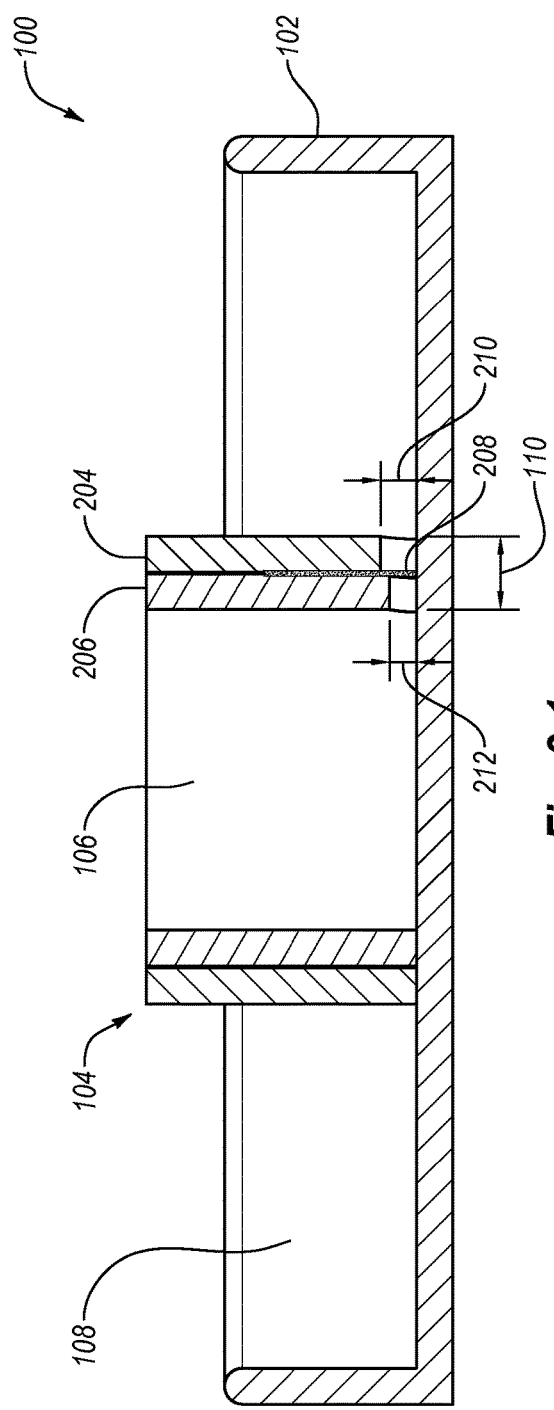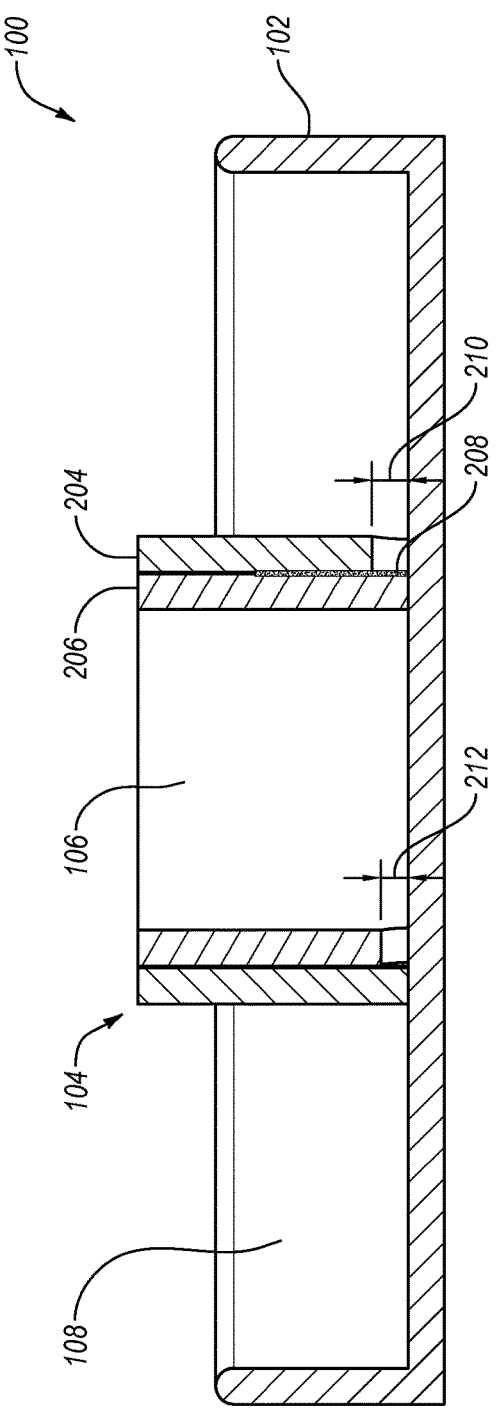

METASTASIS MIMETIC DEVICE

CROSS REFERENCE TO RELATED APPLICATIONS

This application is a U.S. Nationalization of PCT Application Number PCT/US2014/014725, filed on Feb. 4, 2014, which claims the benefit of and priority to U.S. Provisional Patent Application No. 61/849,875, filed Feb. 4, 2013, and entitled "Metastasis Mimetic Device," the entireties of which are incorporated herein by reference.

BACKGROUND OF THE DISCLOSURE

1. The Field of the Invention

Generally, this disclosure relates to test component imaging devices. More specifically, the present disclosure relates to devices, systems, and methods for the culturing and imaging of cells during controlled interaction with a test component.

2. Background and Relevant Art

While recent years have provided improvements in cancer therapies, metastatic breast cancer still results in an 80% mortality rate. Metastatic cancer causes the death of a high percentage of patients because, at least in part, there is a limited set of treatment option due to a lack of understanding of the mechanisms of the disease process. Better understanding of the mechanisms of the disease may lead to improvements in treatment options or the development of additional or alternative treatment options. One of the challenges to understanding the disease mechanics is a tool by which to properly replicate and visualize the metastatic process for investigative purposes.

At present, rodents are the primary methodology to investigate the metastasis process. Unfortunately, apart from being costly and complex, the cell culture systems may be limited to studying signaling pathways and/or one cellular process at a time. Additionally, there are inherent differences between the human and mouse biological systems, compromising the usefulness of a rodent as an analog for the processes occurring in a human. Because metastasis is a multi-stage process, a rodent-based method is unable to fully replicate the cellular behavior throughout the duration of the process.

The process includes carcinoma cells from a tumor migrating along the lymphatic system or through the circulatory system to invade the basement and enter the blood in a process known as intravasion. The exiting of the blood vessels and interacting with other tissues in the body is known as extravasion. The cancer cells may then grow and develop into additional tumors in a process known as colonization.

Metastasis leads to a higher mortality rate in patients due partially to an inability to detect the metastasis events early enough in the process and due partially to an inability to effectively treat and eliminate the metastatic cells.

The limited understanding of the molecular and cellular mechanisms of the metastatic disease inhibits the development of effective therapies and the ability to preemptively diagnose metastatic disease. This underlines the importance of understanding the multi-stage interaction between metastatic cancer cells and healthy tissue cells. Therefore, developments of new technologies to study metastatic disease and test potential drugs may be desirable in order to fully understand the molecular and cellular mechanisms of the disease.

BRIEF SUMMARY OF THE DISCLOSURE

Implementations of the present disclosure address one or more of the foregoing or other problems in the art with apparatuses, systems, and methods for imaging at least two test components and providing controlled interaction between test components.

In one embodiment, a device for the imaging of at least two test components includes a chamber that has a base and at least one wall. The chamber may have an opening with a porous member disposed across the opening and a gate associated with the opening. The opening may allow fluid communication between an interior and an exterior of the chamber. The gate may be moveable relative to the chamber.

In another embodiment, a device for the imaging of cell cultures includes an internal wall and an external wall that define a chamber and are moveable relative to one another. The internal and external walls may have an internal opening and external opening disposed through each, respectively. The internal and external walls may be moveable relative to one another. When the internal and external walls are moved such that the internal and external openings align, the internal and external openings may form a channel providing fluid communication between an interior and an exterior of the chamber. A porous member may be disposed between the internal and external walls such that the porous member covers at least the internal opening or the external opening.

In another embodiment, a method for imaging at least two test components is presented. The method may include providing a device including a chamber that has a base and at least one wall. The chamber may have an opening with a porous member disposed across the opening and a gate associated with the opening. The opening may allow fluid communication between an interior and an exterior of the chamber. The gate may be moveable relative to the chamber and selectively seal the opening. A first test component may be positioned adjacent the opening in the exterior of the chamber. A second test component may be inserted adjacent the opening in the interior of the chamber. The gate may then be moved to allow communication between the first and second test components.

Additional features and advantages of exemplary implementations will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which:

FIG. 3-1 is a cutaway side view of the mimetic device of FIG. 1 with the channel open;

FIG. 3-2 is a cutaway side view of the mimetic device of FIG. 1 with the channel closed;

FIG. 4-1 is a top view of the mimetic device of FIG. 3-1;

FIG. 4-2 is a top view of the mimetic device of FIG. 3-2;

FIGS. 5-1 to 5-3 are top schematic views of a mimetic device in accordance with the present disclosure for selectively isolating test components.

DETAILED DESCRIPTION

One or more implementations of the present disclosure relate to devices, systems, and methods for imaging at least two test components. The device may provide one or more optically clear, biocompatible chambers in which to contain test components. The test components may be selectively introduced to one another via one or more channels having a porous member disposed covering the channel. The porous member may regulate flow across the channel and/or provide a structure upon which a member may be provided to replicate the intravasion and/or extravasion steps of the metastasis process.

Figure 1:
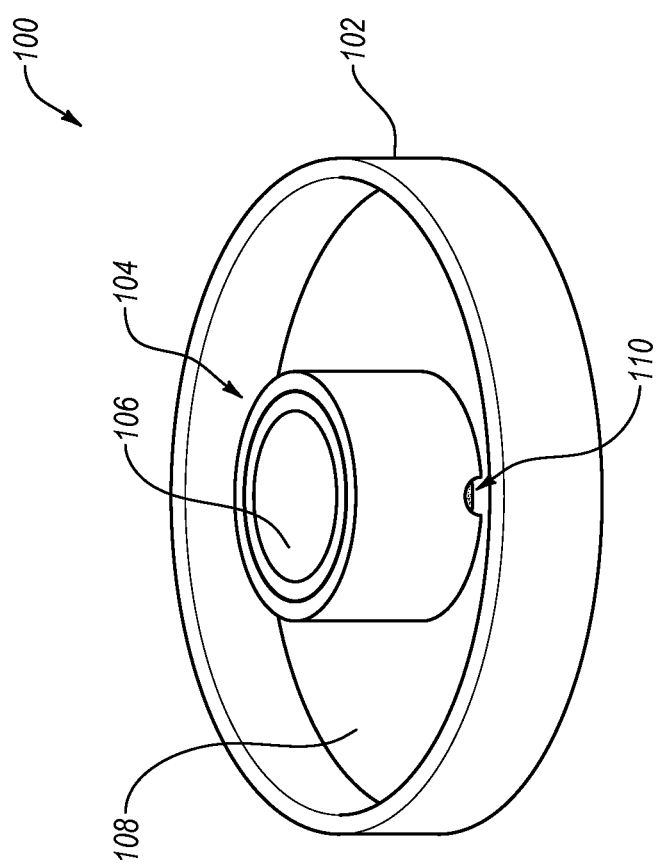
FIG. 1 is a perspective view of a mimetic device in accordance with the present disclosure.

FIG. 1 illustrates a perspective view of a mimetic device 100 according to the present disclosure. Because the mimetic device 100 may need to be used during imaging of organic or inorganic structures contained within, in some embodiments, the mimetic device 100 may comprise a biocompatible material that provides optical clarity with low birefringence and little to no auto-fluorescence sufficient to image cellular growth in the mimetic device 100. In further embodiments, the mimetic device 100 may comprise a material that can withstand standard sterilization techniques such as an autoclave, ethylene oxide, and/or gamma radiation. In a yet further embodiment, the mimetic device 100 may comprise polycarbonate, glass, polysulfone, polydimethylsiloxane, polymethyl-methacrylate, silicone, and/or polystyrene.

The mimetic device 100 may include an outer chamber 102 and an inner chamber 104. In an embodiment, the outer chamber 102 is a circular, walled basin as depicted in FIG. 1. In another embodiment, the outer chamber 102 may be square, rectangular, round or any other suitable shape. The outer chamber may have walls sufficient to retain a fluid within the outer chamber 102. In yet another embodiment, the outer chamber 102 is a Petri dish. In a yet further embodiment, the outer chamber 102 may be 6 centimeters in diameter or 10 centimeters in diameter. The inner chamber 104 of the mimetic device 100 may define an interior volume 106 surrounded by an exterior volume 108. The interior volume 106 and exterior volume 108 may be selectively in fluid communication via a channel 110 disposed through the inner chamber 104, which connects the interior volume 106 to the exterior volume 108. In an embodiment, both the outer chamber 102 and the inner chamber 104 are sufficiently large in volume to contain approximately 2 million cells each. The channel 110 may be selectively sealed by one or more gate structures. In the embodiment depicted in FIG. 1, the gate structure is the rotatable, concentric cylinders described in more detail in FIG. 2. In other embodiments, the gate structure may take other forms.

Figure 2:
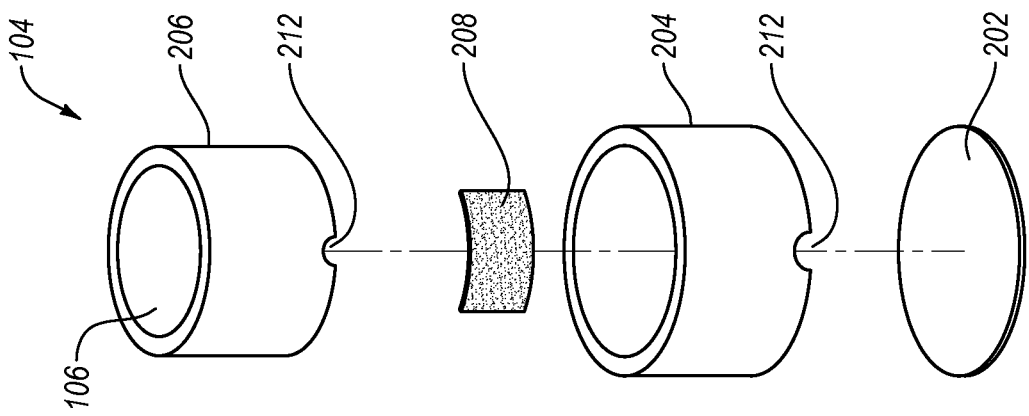
FIG. 2 is an exploded view of the inner chamber of the mimetic device of FIG. 1.

FIG. 2 depicts an exploded view of an embodiment of the inner chamber 104. The inner chamber 104 includes a base 202, an external wall 204, and an internal wall 206. In an embodiment, the base 202 may be a distinct component of the inner chamber 104, while in another embodiment, the base 202 may be a portion of the outer chamber 102 in which the inner chamber 104 is connected. When the base 202 is a distinct component of the inner chamber 104, such as depicted in FIG. 2, the inner chamber 104 may be removable from the outer chamber 102. In such embodiments, the mimetic device may consist only of the inner chamber 104 and be portable between other chambers or basins, as necessary. When the base 202 is a portion of the outer chamber 102, at least a portion of the inner chamber 104 may be at least partially affixed to the outer chamber 102. In such an embodiment, the inner chamber 104 may be affixed to the outer chamber 102 by adhesive, welding, or any other appropriate connection including being formed integrally to the outer chamber 102 during manufacture. In further embodiments, the inner chamber 104 may be otherwise connected to the outer chamber 102. In yet further embodiments, the inner chamber 104 may not be connected to the outer chamber 102, but may simply rest thereon.

While the embodiment depicted in FIG. 1 shows the external wall 204 fixed relative to the outer chamber 102 and the internal wall 206 rotatable relative to the external wall 204 and, therefore, the outer chamber 102, the internal wall 206 may be fixed relative to the outer chamber 102 and the external wall 204 may instead be rotatable. In other words, in embodiments where the external wall 204 and internal wall 206 rotate relative to each other, the external wall 204 or the internal wall 206 may be fixed relative to the outer chamber 102 such that the other wall (external or internal) may move freely. In further embodiments, neither the external wall 204 nor the internal wall 206 may be fixed, but rather both may move freely relative to one another. In a further embodiment, the external wall 204 and/or the internal wall 206 may be fixed to the base 202 or the outer chamber 102 and yet be moveable relative to each other. For example, a recession may be formed in the base 202 or the outer chamber 102 into which the external wall 204 and/or the internal wall 206 may be fixed, though moveable.

In the depicted embodiment, the external wall 204 is disposed around the internal wall 206 such that an inner surface of the external wall 204 is adjacent to an outer surface of the internal wall 206. The external wall 204 and internal wall 206 may have a porous member 208 disposed therebetween.

The porous member 208, in an embodiment, may have porosity such that fluid may pass therethrough, while particles or other substances suspended in the fluid may be selectively restricted from crossing the porous member 208. In another embodiment, the porous member 208 may have a porosity of about 8 microns. In yet another embodiment, the porous member 208 may have porosity less than about 8 microns. In a yet further embodiment, the porous member may have a porosity about 8 microns to about 40 microns. In yet another further embodiment, the porous member may have a porosity of greater than about 40 microns.

The porous member 208 may allow for a coating of endothelial cells, which may mimic part of the blood vessel. In addition, a cell culture medium, such as MATRIGEL, may be applied to the porous member. In this way, the porous member 208 dividing the outer chamber 102 and inner chamber 104 may aid in replicating the intravasion or extravasion steps of the metastasis process. The porous member 208 may comprise a porous polymer. In another embodiment, the porous member 208 may comprise a woven fiber. In yet another embodiment, the porous member 208 may comprise polycarbonate, polystyrene, polyester, or silicon. In a further embodiment, the porous member 208 may comprise fiberglass, carbon fiber or a metal screen.

The porous member 208 extends transversely across the channel 110 that extends through the external wall 204 and the internal wall 206. The porous member 208 may provide fluid communication between the interior volume 106 and exterior volume 108. The channel 110 comprises an external opening 210 and an internal opening 212 with the porous member 208 disposed between the external opening 210 and the internal opening 212.

As shown in the embodiment of FIG. 2, the porous member 208 may be sized such that it is larger than the external opening 210 and/or the internal opening 212. In some embodiments, the porous member 208 may be only slightly larger than the external opening 210 and/or the internal opening 212. In further embodiments, the porous member 208 may be substantially larger than the external opening 210 and/or the internal opening 212. For example, the porous member 208 may be as high as the external wall 204 and/or the internal wall 206. In another example, the porous member 208 may extend around about a third of the inner perimeter (i.e. circumference in a circular case) of the external wall 204 and/or the outer perimeter of the internal wall 206. In a further example, the porous member 208 may at least partially fill an annular gap (not shown) between the external wall 204 and the internal wall 206 (i.e. be the same height as the external wall 204 and/or the internal wall 206 and/or extend around the entire perimeter of the external wall 204 and/or the internal wall 206). In yet a further example, the porous member 208 may completely fill an annular gap (not shown) between the external wall 204 and the internal wall 206 (i.e. be the same height as the external wall 204 and/or the internal wall 206 and extend around the entire perimeter of the external wall 204 and/or the internal wall 206). In still further embodiments, the porous member 208 may be inserted into and/or affixed inside the external opening 210 and/or the internal opening 212.

In the depicted embodiment, the external opening 210 and internal opening 212 have different dimensions, and in particular, the internal opening 212 is smaller in cross-sectional area than the external opening 210. However, in other embodiments, the external opening 210 may have the same cross-sectional dimensions as the internal opening 212. In yet further embodiments, the external opening 210 may have smaller cross-sectional dimensions than the internal opening 212.

Furthermore, the shape of both the external opening 210 and the internal opening 212 are shown as semi-circular in shape. In other embodiments, the shapes of the external opening 210 and the internal opening 212 may differ and/or may be otherwise shaped. For example, the external opening 210 and/or the internal opening 212 may be elliptical, semi-elliptical, polygonal, or otherwise shaped.

The smaller of the external 210 and internal 212 openings may at least partially determine a flow rate through the channel 110. For example, when the internal opening 212 is the smaller of the external 210 and internal 212 openings, the internal wall 206 may be interchangeable with similarly shaped internal walls with internal openings of various sizes. In other embodiments, the internal wall 206 may comprise multiple internal openings 212 of varying cross-sectional dimensions in order to provide a variety of flow rates through the channel 110. In further embodiments, the external wall 204 may comprise multiple external openings 210. In such an embodiment, the multiple external openings 210 may correlate to the multiple internal openings 212 of internal wall 206 or may be uncorrelated.

FIG. 1 depicts the device 100 having a single inner chamber 104, however it should be understood that an embodiment in accordance with the present disclosure may include multiple inner chambers 104, and in some cases may include enough inner chambers 104 to render the device compatible with common microplate formats, such as a 96 well microplate or a 386 well microplate. Such an embodiment may allow the use of a mimetic device in accordance with the present disclosure for high throughput screening in applications such as drug discovery or drug delivery testing. A mimetic device in accordance with the present disclosure may enable the measurement of multiple forms of behavior at the same time on live cells in response to various test components in either a microplate format or in individual devices.

Figures 1, 5:
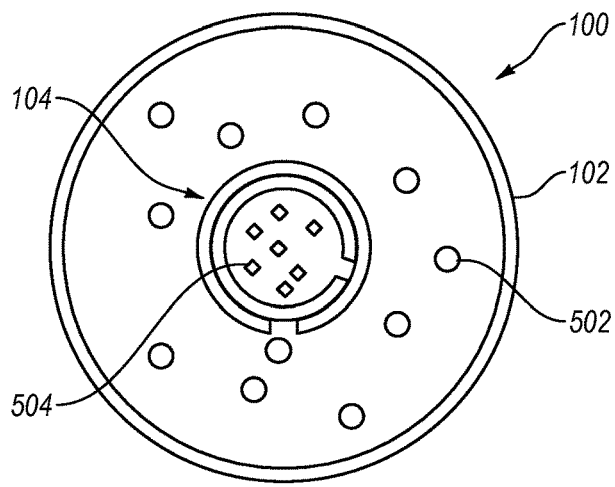
Figures 2, 5:
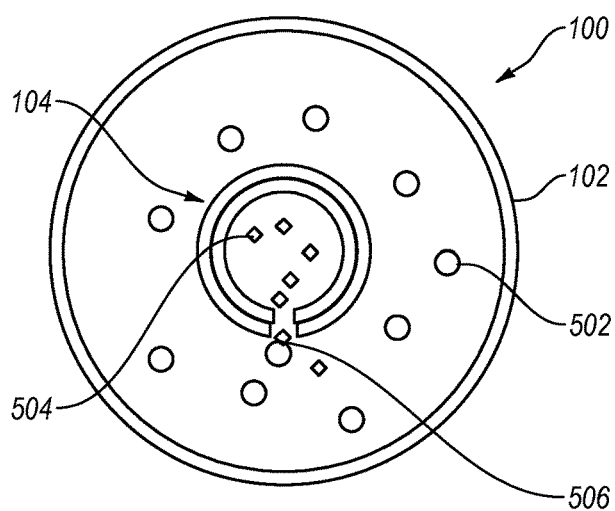
Figures 3, 5:
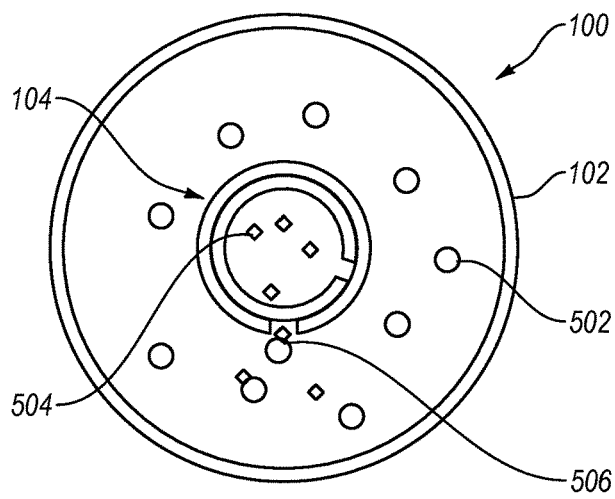

As illustrated in FIGS. 3-1 and 3-2, the internal wall 206 and/or external wall 204 may be rotatable relative to each other. When the internal wall 206 and/or external wall 204 are rotated relative to each other such that the internal opening 212 aligns with the external opening 210, channel 110 is open and may allow fluid communication between the interior volume 106 and the exterior volume 108. As shown in FIG. 3-2, when the internal wall 206 (and/or in other embodiments the external wall 204) is rotated to some other angle (such as the 180-degree rotation depicted) such that the internal opening 212 does not align with the external opening 210, channel 110 is closed and the external wall 204 and/or the internal wall 206 may prevent fluid communication between the interior volume 106 and the exterior volume 108.

Figures 1, 4:
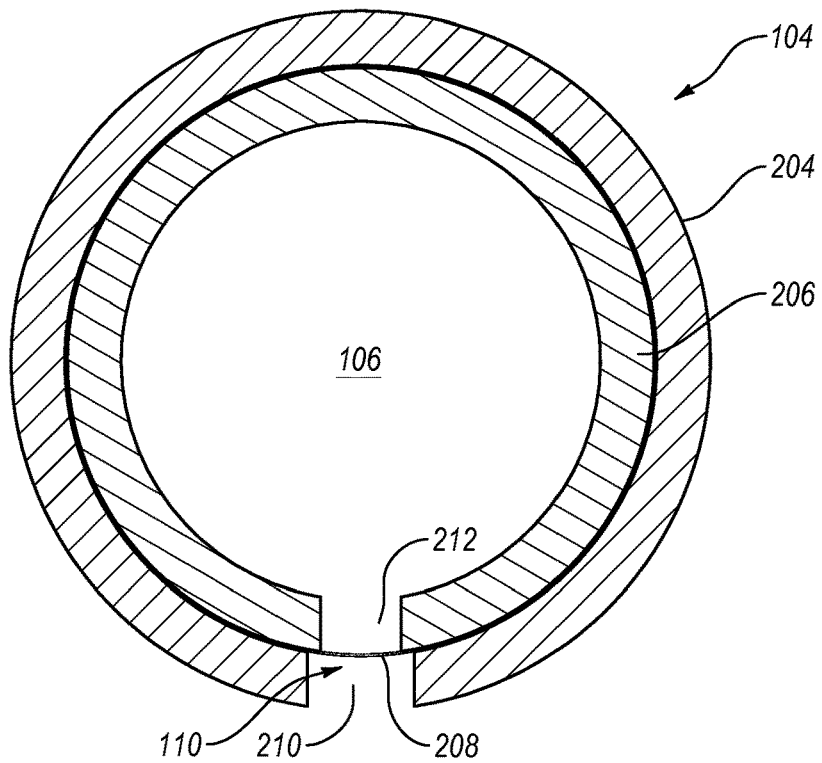
Figures 2, 4:
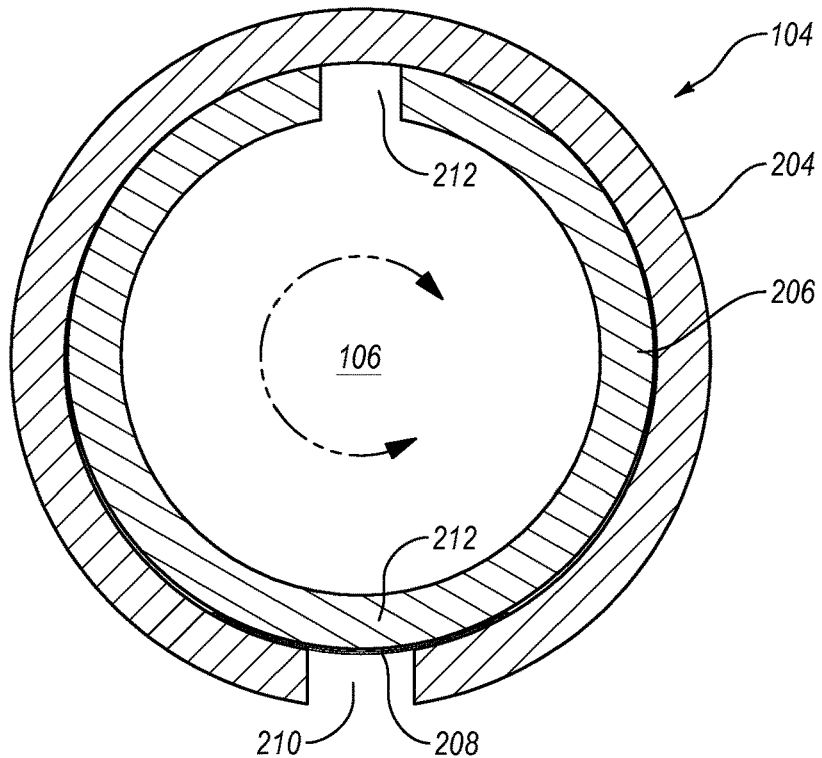

FIGS. 4-1 and 4-2 are top views of FIGS. 3-1 and 3-2. When the internal wall 206 and/or the external wall 204 are rotated relative to each other such that the internal opening 212 aligns with the external opening 210, channel 110 is open and provides fluid communication between the interior volume 106 and the exterior volume 108. The porous member 208 may cover the cross-sectional area of the channel 110. As described above, the porous member 208 may extend around the full circumference of the inner chamber 104, extend only as far as needed to cover the channel 110, or any amount in between. As shown in FIG. 4-2, when the internal wall 206 and/or the external wall 204 are rotated to some other angle (such as the 180-degree rotation depicted) relative to each other such that the internal opening 212 does not align with the external opening 210, channel 110 is closed and the external wall 204 and/or the internal wall 206 prevent fluid communication between the interior volume 106 and the exterior volume 108.

FIGS. 5-1 to 5-3 depict a method of controlled interaction of a first test component 502 and a second test component 504 within a mimetic device 100. As shown in FIG. 5-1, the outer chamber 102 contains the first test component 502 and the inner chamber 104 contains the second test component 504. Each test component 502, 504 may comprise cellular specimens or tissue to be analyzed; growth media; a stimulus, such as a drug, a protein, or cells/tissue; or combinations thereof. FIG. 5-1 illustrates the inner chamber 104 in a "closed position." The first test component 502 is positioned adjacent the opening in the exterior of the inner chamber 104 and the second test component 504 is inserted adjacent the opening in the interior of the inner chamber 104. The first test component 502 is isolated from the second test component 504 by the inner chamber 104. The porous member may optionally be treated with a cellular growth medium, such as MATRIGEL, and/or may have endothelial cells applied thereto.

FIG. 5-2 illustrates the inner chamber 104 in an "open position" after the gate structure, the internal wall as depicted in FIG. 5-2, is moved relative to the external wall of the inner chamber 104 to unseal the opening 110. The channel 110 allows the first test component 502 and second test component 504 to interact 506. In some embodiments, the interaction 506 may occur in the outer chamber 102, may occur in the inner chamber 104, or may occur in both chambers 102, 104. The interaction 506 may be directed by an applied stimulus.

FIG. 5-3 depicts the mimetic device 100 containing the first test component 502 and second test component 504 with the inner chamber 104 returned to a closed position. In such a state as depicted in FIG. 5-3 further isolation is created, after controlled interaction is enabled in FIG. 5-2. Reestablishment of isolation may allow the introduction of additional test components to evaluate the additional test component's effect on the interaction of the first and second test components 502, 504.

In the depicted embodiment, the external wall 204 and the internal wall 206 are concentric cylinders, enabling the rotation of one relative to another. The relative alignment of the external wall 204 and the internal wall 206 form a gate structure that selectively seals the channel 110 extending through the inner chamber 104. In other embodiments, however, the external wall 204 and internal wall 206 may have a different shape, in particular, a shape, such as a square, that does not allow for simple or easy rotation of concentric shapes. In such embodiments, the alignment gate structure may assume a different form, however, while providing similar functionality. In further embodiments, even where relative rotation is contemplated, the alignment gate structure may assume a different form.

Figure 6:
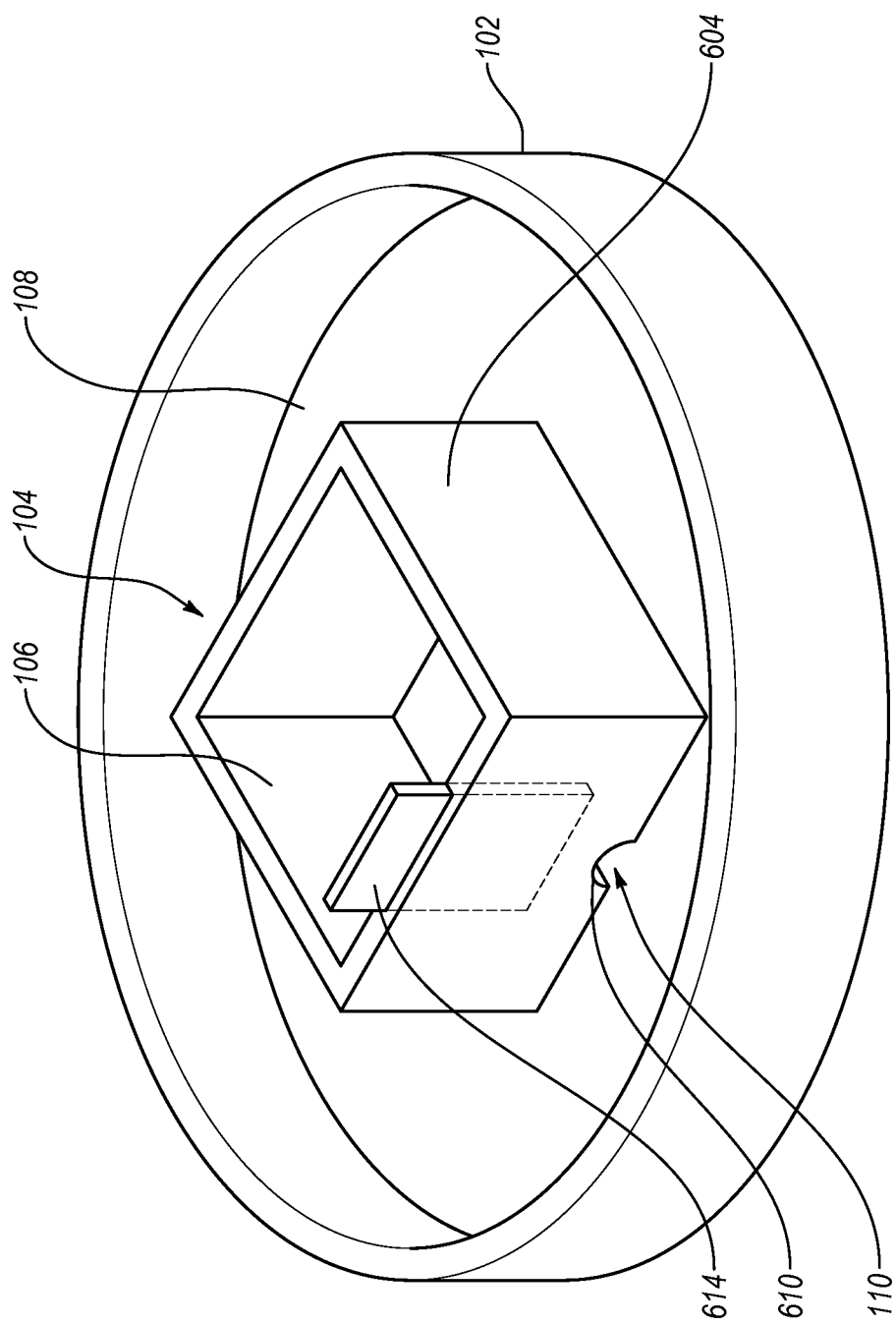
FIG. 6 depicts another embodiment of a mimetic device in accordance with the present disclosure.

In FIG. 6, for example, the inner chamber 104 has a wall 604 that has a polygonal (shown as a square) shape when viewed from the top. Because the wall 604 is a square, a second, concentric wall would not be able to rotate relative to the wall 604 to allow alignment of a second opening with the opening 610. In such an embodiment, the gate structure that selectively seals the channel 110 is a tab 614. The channel 110 is selectively sealable by moving a tab 614 vertically relative to the wall 604 to open the channel 110 and provide fluid communication between the interior volume 106 and exterior volume 108. It should be understood, that while the tab 614 is depicted disposed in a recession of an inner surface of the wall 604, the tab 614 may be disposed inside or outside of a recession, on the inner surface of the wall 604, on an outer surface of the wall 604, or internal to the wall 604.

Furthermore, a tab 614 such as depicted in FIG. 6 is not mutually exclusive with the use of the concentric, rotatable external wall 204 and internal wall 206. For example, a tab 614 may comprise a second porous member allowing the selective introduction of a second porous member to further regulate a flow of material between the interior volume 106 and the exterior volume 108. The tab 614 gate structure of FIG. 6 may be used in addition to any aforementioned embodiment and variants thereof.

While the mimetic device 100 has been described herein as suitable for metastasis cell evaluation, applications for the device are not so limited and may extend to any field of use for which the controlled interaction of test components is desirable. Some example applications may include cardiology, immunology, CNS/neuroscience, Angiogenesis, GI/Metabolism, muscoskeletal applications, and the study or treatment of respiratory processes in humans and other organisms. Other applications may include modeling and testing cellular functions such as cell migration, cell invasion, cell and/or tissue growth, cell and/or tissue survival, cell and/or tissue differentiation, interactions between cells, interactions between individual cells and tissue, and/or interactions between cells and proteins. Applications may further include studying the function of biological structures including the blood brain barrier, blood vessels, or the functions of other organs or tissues; the development of biological structures including skeletal structures, the blood-brain barrier, blood vessels, the lymphatic system, or other organs or tissues; chemical/biochemical processes; fluid dynamics; viscosity; temperature gradients; and/or chemical reactions. Additionally, the device 100 may be applicable to botany for the study of plant breeding, biodiversity, genetics, and/or nutrition, as well as the study of prokaryotic organisms such as bacteria.

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A device for imaging at least two test components, the device comprising:
   a chamber having a base and at least one wall that define an interior and an exterior of the chamber;
   an external opening through the at least one wall of the chamber, the external opening adjacent the base of the chamber, the external opening having an upper surface in the at least one wall and being defined by the upper surface, the external opening configured to provide fluid communication between the interior and exterior of the chamber;
   a gate moveable relative to the chamber and configured to selectively seal the opening; and
   a porous member disposed transversely across the external opening.

2. The device of claim 1, wherein the at least one wall is a first cylinder.

3. The device of claim 2, wherein the gate is a second cylinder having an inner opening therethrough, the second cylinder being disposed concentrically to the first cylinder.

4. The device of claim 1, wherein the gate is rotatable relative to the chamber.

5. The device of claim 1, wherein the chamber or the gate are formed from polycarbonate, polysulfone, polydimethylsiloxane, polymethyl-methacrylate, silicone, or polystyrene.

6. The device of claim 1, further comprising a second porous member selectively disposed across the opening.

7. The device of claim 1, further comprising multiple external openings through the at least one wall of the chamber.

8. The device of claim 7, wherein the gate includes multiple internal openings, wherein at least two of the multiple internal openings are correlated with at least two of the multiple external openings.

9. The device of claim 1, wherein the gate includes multiple internal openings.

10. The device of claim 9, wherein each internal opening of the multiple internal openings opens into one of a plurality of internal chambers.

11. The device of claim 1, wherein the gate includes an internal opening, the internal opening and the external opening being semi-circular in shape.

12. The device of claim 1, wherein the gate includes an internal opening, the internal opening having about the same or greater cross sectional dimensions as the external opening.

13. The device of claim 1, wherein the porous member is disposed in an annular gap between the at least one wall of the chamber and the gate.

14. The device of claim 13, wherein the porous member fills more than a third of the annular gap.

\* \* \* \* \*